United States Patent [19]

Bird, Jr. et al.

[11] 4,293,217
[45] Oct. 6, 1981

[54] CONTINUOUS-FLOW CONDENSATION NUCLEI COUNTER AND PROCESS

[75] Inventors: Alvin N. Bird, Jr.; Norman L. Francis; Albert L. Thomas, Jr., all of Birmingham, Ala.

[73] Assignee: The United States of America as represented by the Secretary of the Army, Washington, D.C.

[21] Appl. No.: 118,946

[22] Filed: Feb. 6, 1980

[51] Int. Cl.³ .............................................. G01N 1/00
[52] U.S. Cl. .................................. 356/37; 73/863.11
[58] Field of Search .................. 73/421.5 R, 421.5 A, 73/28; 356/37; 261/103, 97

[56] References Cited

U.S. PATENT DOCUMENTS 2,956,435  10/1960  Rich ...................................... 356/37
3,462,609  8/1969  Beattie ................................. 356/37
3,679,369  7/1972  Hashimoto ........................... 261/97
3,738,751  6/1973  Rich ...................................... 356/37

*Primary Examiner*—S. Clement Swisher
*Attorney, Agent, or Firm*—Nathan Edelberg; Robert P. Gibson; Richard B. Dence

[57] ABSTRACT

A portable device and a process for detection of persons and things by the "Condensation Nuclei" technique. The disclosure sets out a new continuous flow device and process that collects an air sample, subjects it to supersaturation conditions when flowing for growing or condensation on air sample nuclei, and detects and counts the condensated or grown particles with a photo means and a conventional counter. An air sample is pumped through a heated tube humidifier where the sample becomes supersaturated for condensation. It is then carried by detector means for counting.

6 Claims, 6 Drawing Figures

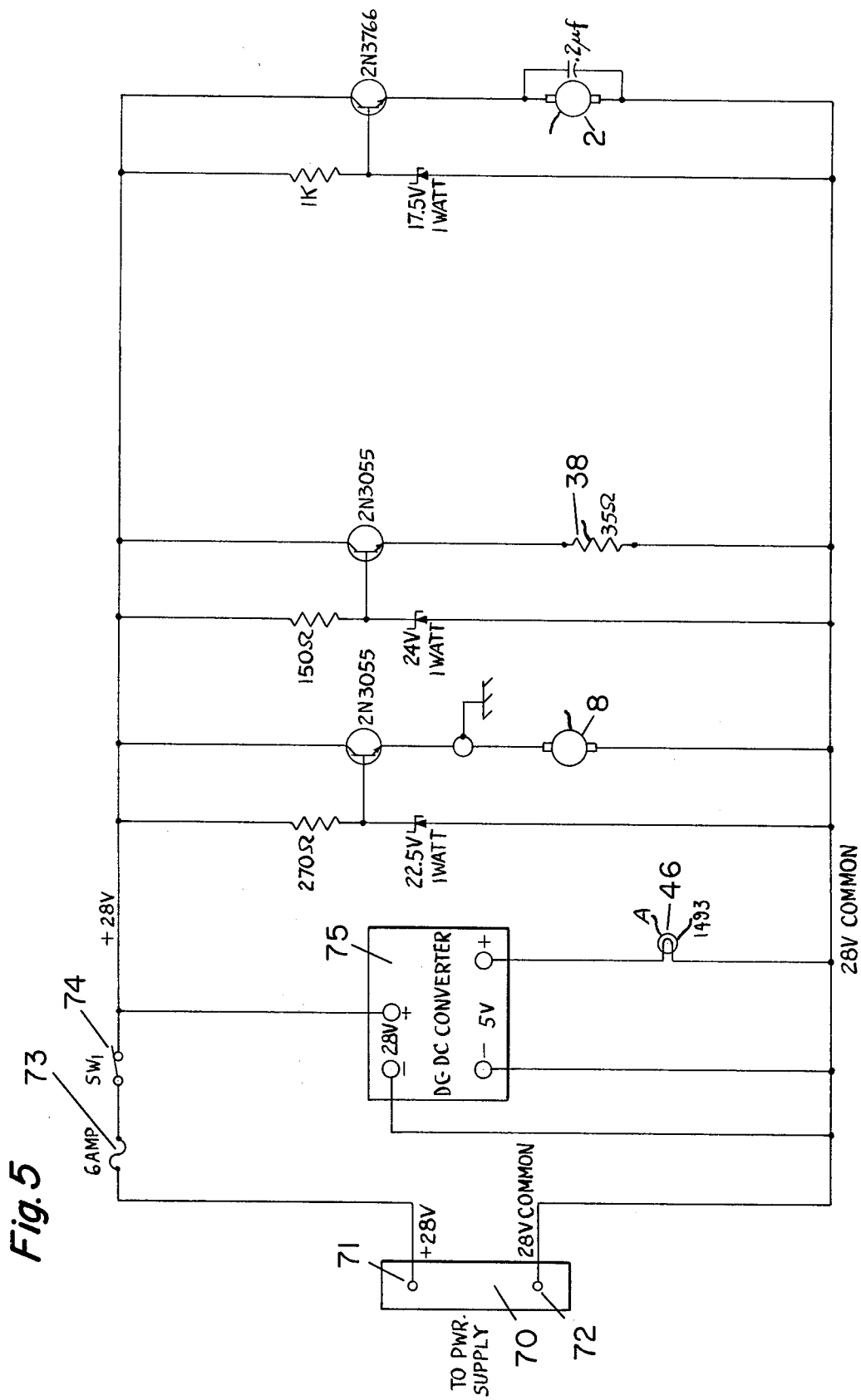

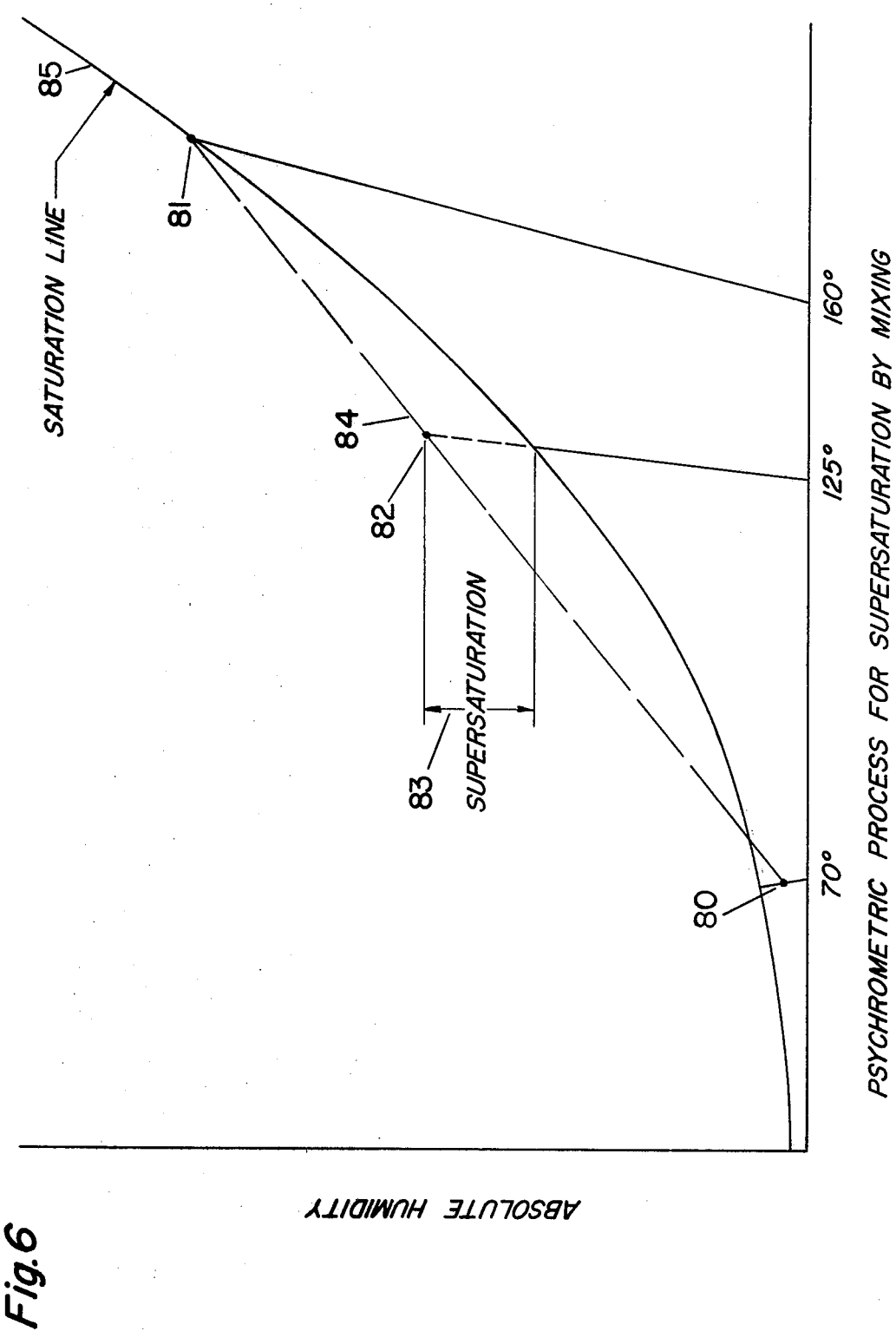

CONTINUOUS-FLOW CONDENSATION NUCLEI COUNTER AND PROCESS

DEDICATION CLAUSE

This invention may be used by and/or for the U.S. Government without the payment of any royalties thereon.

BACKGROUND OF THE INVENTION

Our invention deals with condensation nuclei particles detection. Since World War II, interest has been directed cyclically to various uses for condensation nuclei for detection purposes. It involves the phenomenon of using humidity to condense or form fog or cloud components upon and around small particles in the atmosphere. Once this localized fog or cloud forms, detection can be had therefrom. Ninety-five percent of discernible condensation nuclei that can be beneficially used in this manner are the results of some form of combustion. These particles are generally submicroscopic in size and will act as nuclei for the condensation of water and therefore these particles are often referred to as Condensation Nuclei (CN). When conditions of supersaturation are properly controlled, this condensation will occur rapidly and particles as small as 0.001 um diameter will grow to water droplets that are five to ten um in diameter. This growth phenomenon provides an extremely sensitive technique for the detection of submicroscopic sized particulate matter in the atmosphere. The concentration of water droplets produced by condensation is easily measured by a standard light-attenuation or light-scattering photoelectric system.

Detection of the submicroscopic particles found first use in World War II when atmospheric monitoring occurred for submarine detection. In this instant, the then only internal combustion engine made of submarine power released these submicroscopic particles during the period of surfacing and battery recharging. Hence, vapor trails were created and sought by detection.

In the 1960's, the Army made application of "CN" detection by way of personnel detection, i.e., invisible plumes of "CN" caused from engine exhausts, fires, and other forms of combustion in and about personnel.

In the time frame of our invention activities, "CN" detection methods have also found their way into endeavors extending from monitoring computer rooms to air pollution and air quality measurement methods. Along with these above mentioned uses of "CN" detection, numerous detector units have been developed of varying designs. Each of these type units have in common the Aitken nuclei counter principle. This is a well known process of taking a sample, humidifying it, expanding it, and measuring the concentration of condensation nuclei at a rate of several times per second.

In an Aitken nuclei counter device, a sample of air is subjected to rapid expansion to a low pressure. The drop in temperature during adiabatic expansion induces condensation of the humidity in the air around the condensation nuclei. The size of particles upon which condensation occurs depends upon the degree of supersaturation caused by the expansion; and, to some extent, on the chemical properties of the particles. All of these Aitken type devices use expansion to produce supersaturation and the attendant growth of the nuclei by condensation.

The Aitken method is a non-continuous flow sample type process which requires complex, cumbersome and expensive mechanical apparatus of high vacuum capacity which is plagued by a multitude of maintenance problems. Most of the apparatus is of the non-portable type, thereby hampering detector utility.

A long-felt need has existed for a small, compact "CN" unit and process with constant measuring features. However, until our invention, no success has been had in this area. It appears that the Aitken principle has set the parameters for the field and impeded innovation thereby.

SUMMARY OF THE INVENTION

Briefly, our invention deals with a process and a system or device for the measurement of the concentration of condensation nuclei in a continuous manner. With our "CN" invention process and device, we have substantially eliminated the need for expansion while still having the needed supersaturated feature for condensation. It is done by locally heating water to the vapor stage and contacting with it a continuous flow of a gaseous sample material such as air containing microparticles, for example. The ratio of vapor to samples should be such that a supersaturation condition originally occurs as the sample mixes with the vapor. Then, because the gaseous sample is cool, condensation commences. The condensation forms about the nuclei or particles and they become visible. This is commonly called "growing." Once the particles are visible, they can be optically detected and counted by use of a light beam, photocell, and amplifier. The water is pumped to a humidifier and locally heated as by an electrical heater means, for example, while contemporaneously pumping sample gas containing micro-particles through and about the humidifier. This is that for which we seek Letters Patent.

It is therefore an object of our invention to provide a new process and device for condensation nuclei detection by continuous sampling.

It is a further object of our invention to provide a new process and device for condensation nuclei detection by continuous sampling without substantial expansion.

It is further still an object of our invention to provide a new process and device for condensation nuclei detection by continuous sampling without substantial expansion by local heat vaporization and sample contact.

Another still further object of our invention is to provide a new process and device for condensation nuclei detection by continuous sampling without substantial expansion by focally heating for humidification and sample contact therewith and then cooling same.

Other objects and advantages of the invention will be readily apparent to one ordinarily skilled in the art as he peruses the remainder of the specification and drawings.

THE DRAWINGS

FIG. 5 is an electrical schematic diagram of our invention.

FIG. 6 is a humidity vs. enthalpy curve of a conventional direct mix technique.

SPECIFIC EMBODIMENT

Figure 3:
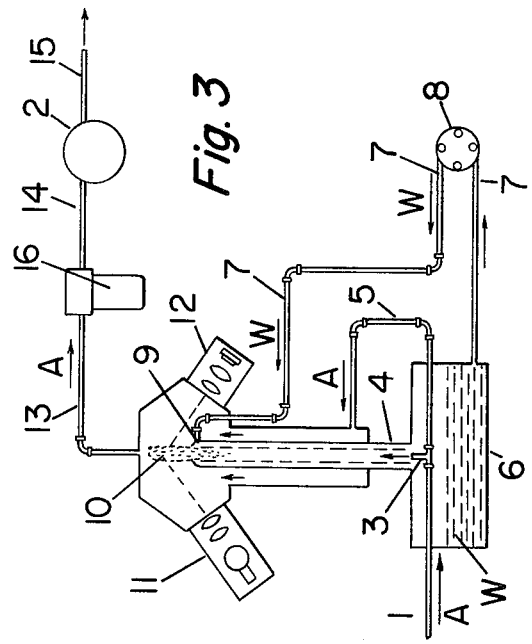
FIG. 3 shows our Condensation Nuclei Detector system.

Referring to FIG. 3, we depict our detector assemblage and system. Inlet air or sample air is drawn through pipe 1 lower left in the direction of arrow A by way of air pump 2 depicted upper right. The air sample is separated at tee 3 into two components. One sample component is pulled through humidifier 4 and the other is drawn through pipe 5 along side of the humidifier and functions as body or purging air. Water reservoir 6 containing water "W" is pumped through piping 7 by way of water pump 8 to the top most portion 9 of humidifier tube 4. Here, at a flow rate slightly faster than the evaporation rate, the water W is pumped by pump 8, which is a peristaltic type pump. Though it is understood that other types of pumps will work as well. Upward of humidifier 4 is fog plume area 10 into which condensation nuclei "growth" occurs. To enable counting of the nuclei or particles as growth occurs and as the fog is caused to flow by lamp assemblage 11 projects light on fog plume area 10 so that photodiode 12 and its associated optics can detect the grown particles. Once the particles have been counted, the resultant sample-condensate is exhausted through pipe 13, through condensation filter 16, on through pipe 14 to air exhaust pump 2 and then out exhaust pipe 15.

Figure 1:
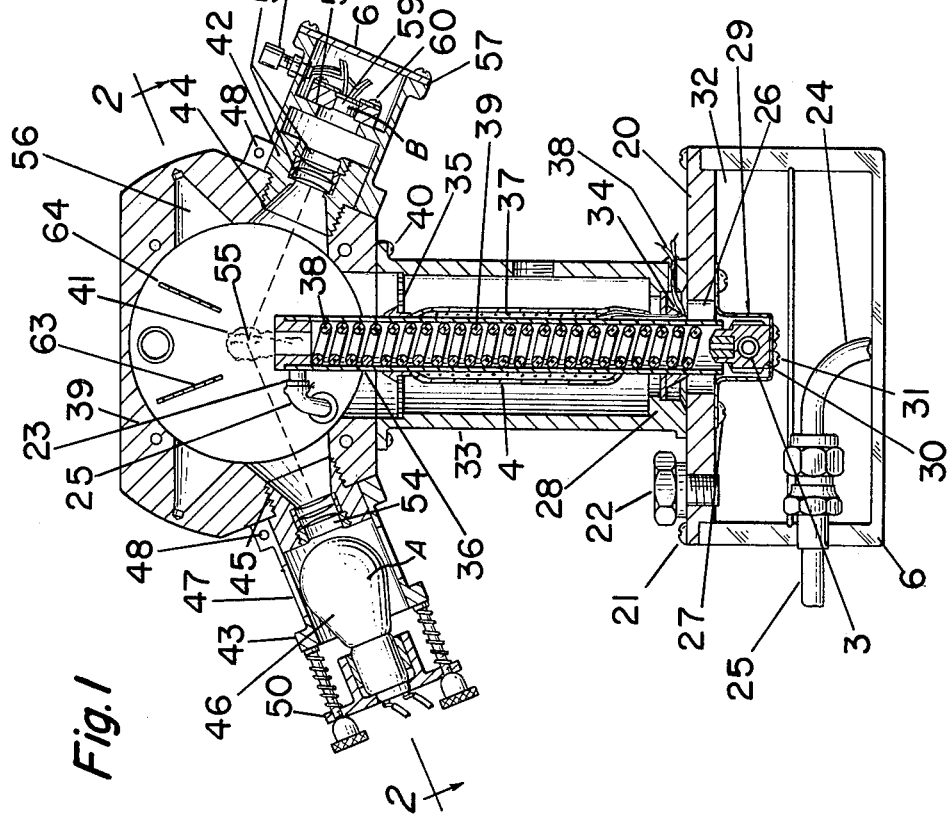
FIG. 1 is a section view of the Condensation Nuclei Detector.

Referring to FIG. 1, we show for simplicity a general section of our Continuous Flow Condensation Nuclei Counter without the motors, piping, casing, and electrical interconnections. Lowermost is reservoir 6 with cover 20 secured thereto with screws 21 sealably securing it thereto with a conventional heat resistant gasket or ring (not shown) interposed. For water fill purposes, screw plug 22 is provided for ready wrench removal. For supplying water to the top of humidifier 4 at inlet 23, piping 25 shown in two segments is connected with removable pickup probe 24. The segments 25, in actuality, are connected together though shown unconnected. Interposed between segments 25, not shown, of course, is water pump 8, aforementioned, with reference to FIG. 3. Mounted spacially within aperture 26 of cover 20 is humidifier tube 4. It is oriented vertically for optimum efficiency and is screw-mounted by way of screws 27 which threadably hold the end of flange 28 of humidifier assembly 33 to cover 20. Though not shown, the interface between flange 28 and cover 20 must be liquid and gas impermeable. Hence, a high temperature gasket in the form of cement, flat gasket stock, or "O" ring material is contemplated for use here. Feeding air to humidifier heater 4 is by way of pipe 1 and tee 3 which are supported by support block 30 held to support hanger 29 by support hanger screws 31 which are threaded to block 30. Pipe 1 passes through (in a sealed manner) back wall 32 at a point not shown. Various commercially available heat resistant hardenable sealants will suffice to provide a seal at back wall 32 where pipe 1 passes through. Also, various fittings, and couplings could be used as well.

The humidifier of FIG. 1 shall now be described. Humidifier heater tube assembly 4 is centerly disposed within outer humidifier body 33 by lower plate 34 and upper apertured plate 35. Lower plate 34 should preferably create a seal with the inner portion of outer body 33 and the outer portion of heater assembly so that no blow back occurs, for example. That is, a back pressure on an incoming air or gas sample could cause unwanted oscilations at or on water being pumped to fitting 23 of humidifier heating tube assembly 4. Tube 36 is stainless steel thin wall tubing that has been chosen because of its corrosive resistance, i.e., the vapor readily corrodes most metals. To the exterior of tube 36 conventional resistance heater wire is wound, bonded, and encapsulated, as with Epoxy 37 or other well known insulative bonding material. Resistance wire connections 38 extend externally from body 33 in a sealed manner. Internally of tube 36 cotton cord 39 is spirally wound to function as the wick of the humidifier. Cord 39 is wound on a stainless steel core wire 39A prior to being disposed within tube 36. Tube 36 extends up and beyond outer body 33 to enable the condensation loaded air sample to be more confined as it progresses upwardly and beyond the illuminator and optical detector means without mushrooming and clouding the illuminator bulb or optical detector lense, for example.

Plume and photo meter chamber of body 39 is affixed by screw means 40 to the upper flange end of humidifier outer body 33. It is the chamber through which "grown" nuclei in plume 41 is detected. Detector assemblage 42 shown threaded thereto at insert 44 and Illuminator 43 threaded thereto at insert 45 are the other components to the photometer.

Figure 2:
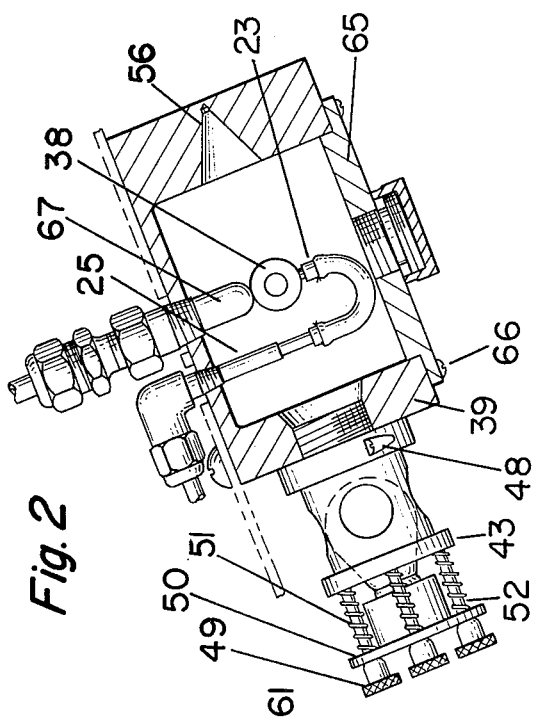
FIG. 2 is a section taken at 2—2 of FIG. 1 showing the condensation chamber, light source, water piping and end of the humidifier of our invention.

Illuminator 43, FIGS. 1 and 2, provides light for detection and contains lamp 46 for light purposes. It is a number 1493 Lamp conventionally used in the field for this type of illumination purpose. Illuminator housing 47 is clamped to assembly 45 by screw 48 shown in FIG. 1 as a circle and in FIG. 2 as a screw head. For illumination adjustment purposes knurl nuts 49 in a trangular array function as final adjustment means. They work like a transit or level trangular adjustment would. Bulb support member 50 is held outwardly by compression springs 51. It is readily seen that with the screw apertures larger than the threads of screw studs 52, member 50 is pressed against the bottom of each of the knurl nuts by springs 51, hence, any knurl nut movement causes adjustment. Bulb 46, a bayonet type, is insulatively supported by sleeve-like receptacle 53 in a conventional fashion. Forward of bulb 46 within insert 45 are disposed optic members 54 which concentrate the bulb light and cause it to converge and traverse point 55. This is the line of sight intersection of the light beam of bulb 46 and the optical image gathering point for detector 42. Point 55 is located as shown in FIG. 1 in plume 41 and is the centroid of the image and beam cross-section. Optics 54 provide a light magnification factor of two and illuminate plume 41 so that a sensitive volume designed to cover a stream of a 5 mm diameter is had. Diametrically opposite bulb 46 in the chamber of body 39 on line of sight thereof, is light trap 56. Light Baffles 63 and 64 for isolating the beam are set out thereabove. Lenses 54 found to be workable with body 39 which has a 2 and ¾ inch diameter internal bore and is of 2 or more inches of depth, are of the achromatic type. The outer lense for both illuminator 43 and detector 42 is 12 mm in diameter and possessed of a 17 mm focal length. The inner lense for each is 13 mm in diameter and has a 51 mm focal length.

Referring now to the right most portion of FIG. 1, detector 42 shall be described. Housing 57 contains a set of lenses 54 as afore described. Housing 57 is clamped to insert 44 by way of screw 48. Disposed rearward of lenses 54 is housing flange 58 to which is secured detector light pin - 50 diode 59 (purchased from United Detector Technology) by screw means 60. Coaxial connector 61 is the means for taking the output of detector diode 59 to appropriate indicating and/or recordation equipment, not shown. Housing cap 62 functions to close off the end thereof and act as an access means for the repair and/or replacement of diode 59.

Referring now to FIG. 2, as aforementioned, it is a section along section line 2 of FIG. 1 depicting Body Chamber 39 looking substantially axially at the upper end of heater tube 38. Lowermost in FIG. 2 is chamber front cover 65 (with view port 68) which is secured with screws 66 to chamber 40 in a sealed fashion with the use of a conventional heat and vapor resistant gasket not shown. Body 39, cover 65, housing 43 and 42 are made of anodized aluminum. Though it is understood, other materials, either coated or uncoated, which will withstand, without deterioration, supersaturated moisture conditions and 200°–300° F. will work well. For exhausting the humid air containing the grown nuclei, exhaust scoop 67 of ⅜ O.D. black plastic tubing is provided.

Referring to FIG. 6, we show a conventional absolute humidity versus enthalpy psychrometric chart. It illustrates the supersaturation technique of direct mixing. Though, it does not exactly represent our system because our process and apparatus involve the simultaneous evaporation and mixture of air in a continuous fashion over the entire length of the heater, it is generally representative.

On FIG. 6 grid, mixture of two masses of air will lie on a line 84 between the points 80 and 81 representing the humidity conditions of the two masses; and the location of the state point representing the mixture will lie at a point dividing the line into segments proportional to the masses of the original parcels of air. Therefore, if a sample of air at 70° F. and 50% relative humidity at point 80 were mixed with a cloud of saturated air at 160° F. point 81 on saturation line 85, the mixture would lie somewhere on the line between the two, depending on the relative amount of each. At about a fifty-fifty mix, the mixture would be about 125° F. (Point 82) and would be sufficiently supersaturated to initiate condensation on particles as small as about 0.01 um diameter as evidenced by supersaturation distance line 83.

In the apparatus and process described in this invention, evaporation of water and mixing of sample air occur simultaneously and continuously over the entire length of the humidifier column or tube 36; therefore, FIG. 6 does not explain the complete humidification process. The mixing process requires additional time and additional moisture for growing the nuclei to their final size and the continuous humidification used in this invention provide both additional time and additional moisture as the sample air moves through the humidifier.

Referring now to FIG. 5 applicants show their electrical schematic diagram. Leftmost, is depicted terminal block 70 with terminals 71 and 72 shown thereon representing a positive 28 volts direct current and a common, respectively. The power supply not shown can be of any form so long as its output exceeds 200 watts safe and continuous load. The device is fused with a 6 amp fuse 73, and is provided with a conventional on-off switch 74. To provide power to lamp 46 of illuminator 43 of FIG. 1 DC to DC converter 75 is provided to provide a 5 volt supply to "1493" lamp 46. This converter is a conventional Arnold Mag. DC-DC converter. Air pump motor 2, a Globe #BD100A104-11 type with its controls, 35 ohm heater wire 38 its associated controls, and water pump motor 8, a Globe SS43A109, model and its controls are also shown.

Figure 4:
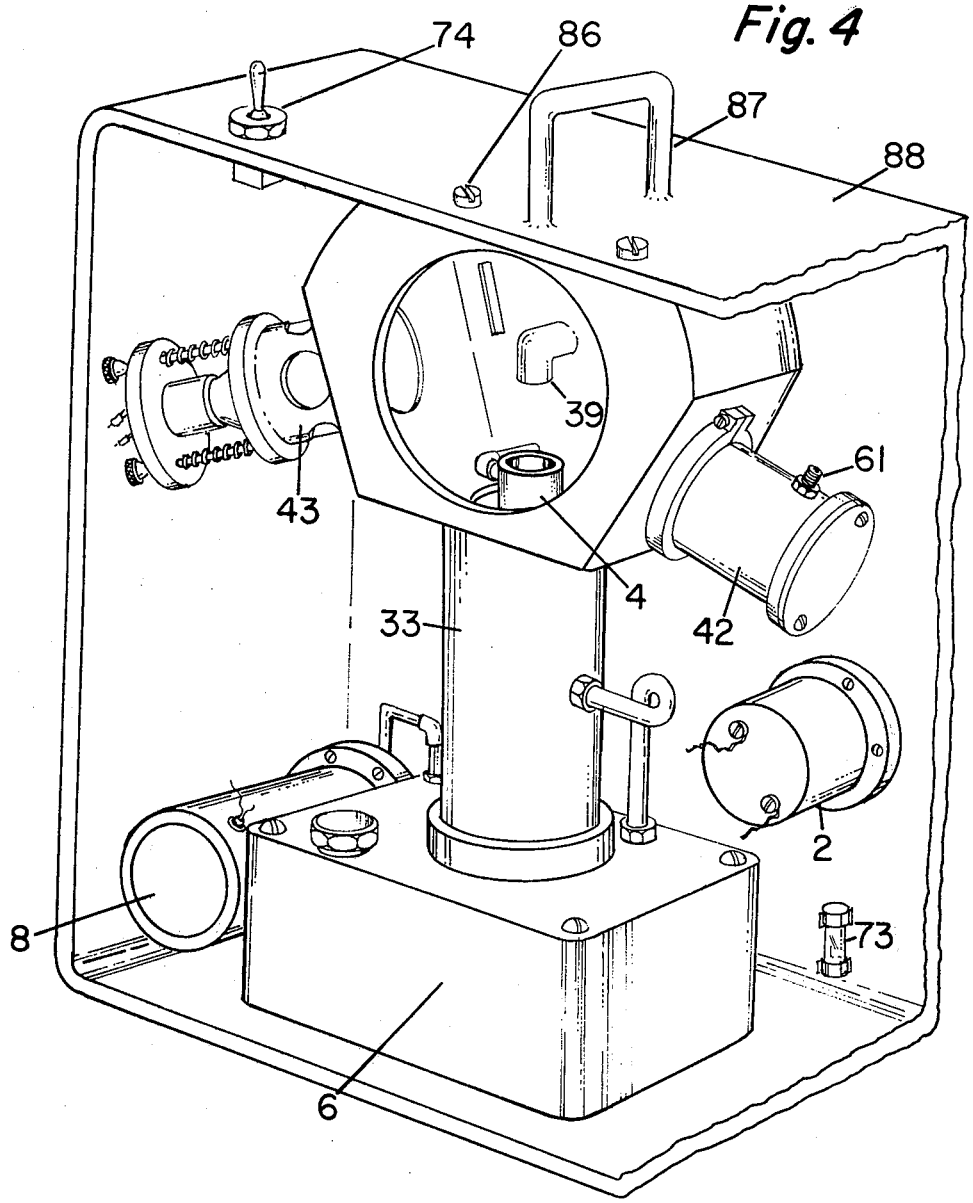
FIG. 4 is an isometric of our Condensation Nuclei Detector System.

Referring now to FIG. 4, we show our continuous flow nuclei detector assemblage mounted in case 88 having handle 87. Water pump 8 is mounted leftmost of reservoir 6 and is connected to supply water at the upper end of humidifier tube 4 at pipe 23 in the chamber of housing 39. Motor 2 for drawing air through the system is shown as being mounted on the right of photo diode 42. Fuse 73 is located below motor 2, however, its location is not critical. Though more vividly shown in FIG. 1, outer humidifier body 33 is shown securely mounted to reservoir 6. Body 39, secured to humidifier outer body 33, is shown as being held fast to case 88 by screws 86. Front cover 65 shown in section in FIG. 2 is not included so that scoop 67, baffle 64 and humidifier tube 46 inside of the chamber could be illustrated. Illuminator 43 is depicted on the left side of body 39. All the electrically operated components, are depicted with wires hanging, though it is understood that each is interconnected as shown in FIG. 5.

OPERATION

To operate our device (see FIG. 4), we first place switch 74 in the "on" position. Referring to FIG. 5, once switch 74 is "on", power is applied to motors 2 and 8, to humidifier heater 4, to illuminator bulb 4 and to photo diode assembly 42. For proper operation, the temperature of the humidifiers, the water flow rate, the sample air destined for flow through the humidifier heater 4, and body air flow for purging the plume should be constant. Tube 4 is heated to between 140°–160° and water pump 8 pumps water W through tube 7 out element 23 into the uppermost portion of humidifier tube 4 to enable it to flow downward, the length of the humidifier along the wick 38 over the heated coils. The wick assures moisture at all times over the coil area. Any excess water flows back to reservoir 32. As pump 8 continues to keep the water flowing over the heated coils, air pump 2 is pulling inlet air into the system which is being separated at tee 3 into sample containing air for flow through tube 4 and body air "A" for purging which flows outside tube 4. As sample containing air enters the lower portion of tube 4 it commences to contact the moisture on the wick and starts to become heated. As air pump 2 continues to move the air upwardly, it gradually becomes supersaturated. When that occurs, it commences to condense. The condensation occurs around nuclei or particles in the air sample and become larger. When the condensing air sample reaches plume 41, the nuclei have "grown" so that illuminator 43 can furnish appropriate illumination to enable detector 43 to detect same. The detected "grown" nuclei can be measured by conventionally used indicating and recording equipment. Once the "grown" nuclei or cloud has passed the detector in the plume chamber, it is drawn along with body air through piping 13 and 14 by pump 2 and then exhausted through pipe 15. Hence, it is seen that the instant invention device can operate continuously and enable the performance of an accurate and continuous condensation nuclei counting process.

Other modifications are possible by varying the types of pumps, fluid flows, temperatures, etc. in light of the teachings herein and are deemed a part of the disclosed and claimed invention.

What is claimed:

1. A portable continuous-flow device for detecting and counting nuclei in sampled air, said device comprising:

an upstanding tubular humidifier housing;

an upstanding and axially elongated humidifier tube centrally disposed within said humidifier housing and cooperating with said humidifier housing to define an annular passageway therebetween in which to accommodate an upward flow of a portion of a continuous flow of sampled air; said humidifier tube defining a longitudinal interior passageway therewithin in which to accommodate an upward flow of another portion of the said continuous flow of sampled air;

means for continuously delivering a forced upward flow of nuclei containing sampled air to a lower region of said annular passageway and a lower region of the interior passageway in said humidifier tube;

a wetted wick disposed within the interior passageway in said humidifier tube for saturating the portion of the continuous upward flow of sampled air therewithin;

means for heating the continuous upward flow of saturated sampled air within said humidifier tube to a temperature higher than the portion of sampled air with said annular passageway between said humidifier tube and humidifier housing;

a plume chamber communicating with the upper regions of the interior passageway in said humidifier tube and the upper regions of annular passageway between said humidifier tube and said humidifier housing, said plume chamber thereby receiving therein both of the aforementioned upwardly flowing portions of sampled air and whereby the heated and saturated portion of the sampled air flowing upwardly from within said humidifier tube is caused to mix with and condense upon airborne nuclei by the portion of sampled air flowing upwardly from within said annular passageway;

means for illuminating said plume chamber to illuminate the condensation nuclei;

means for detecting and counting the illuminated condensation nuclei;

means for continuously exhausting the condensation nuclei from said plume chamber; and a manually transportable enclosure means for mounting each of the foregoing in operative assembled relationship within said enclosure means.

2. A process for continuously detecting and counting nuclei in sampled air by use of manually portable means, said process comprising:

continuously withdrawing a stream of sampled air;

forcefully and continuously flowing separate portions of said stream upwardly along individually confined and noncontacting paths of flow disposed one within the other;

continuously saturating and heating one of said portions of said stream to a higher temperature and moisture laden content than the other portion thereof while said portions are individually confined in said paths of flow disposed one within another;

continuously merging said last-mentioned paths of flow into a single upward flow within a confined chamber to thereby cause said moisture laden portion of said stream to be cooled by the other portion thereof and to cause moisture in the moisture laden portion to condense within said chamber upon nuclei carried by both of said portions of sampled air; and subjecting the resulting condensation carrying nuclei to exposure to illumination and photometric detection within said chamber while continuously exhausting the merged portions of said stream from said chamber.

3. The process as defined in claim 2, wherein said process is carried out in a self-contained manually portable unit.

4. The device of claim 1 wherein the wick is of cotton around a helically disposed steel core material.

5. The device of claim 4 including an air pump secured within said enclosure means for pumping said sampled air continuously.

6. The device of claim 5 including a water pump within said enclosure means for continuously pumping water for said wick.

* * * * *